United States Patent
Bruder et al.

(10) Patent No.: US 7,443,945 B2
(45) Date of Patent: Oct. 28, 2008

(54) METHOD FOR SCATTERED RADIATION CORRECTION IN THE CASE OF AN X-RAY CT, AND X-RAY CT FOR APPLYING THIS METHOD

(75) Inventors: Herbert Bruder, Höchstadt (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/790,709

(22) Filed: Apr. 27, 2007

(65) Prior Publication Data
US 2007/0253524 A1    Nov. 1, 2007

(30) Foreign Application Priority Data
Apr. 28, 2006   (DE) .................. 10 2006 019 923

(51) Int. Cl.
*A61B 6/00*    (2006.01)
(52) U.S. Cl. .............................. 378/7; 378/9
(58) Field of Classification Search .............. 378/4–20, 378/901; 250/370.08, 370.09
See application file for complete search history.

(56) References Cited

U.S. PATENT DOCUMENTS

| | | | |
|---|---|---|---|
| 7,039,153 B2 | 5/2006 | Bruder et al. .............. | 378/9 |
| 2006/0008046 A1 | 1/2006 | Ruhrnschopf .............. | 378/7 |
| 2007/0253525 A1* | 11/2007 | Popescu .................... | 378/7 |

FOREIGN PATENT DOCUMENTS

| DE | 103 02 567 A1 | 8/2004 |
|---|---|---|
| DE | 10 2004 029 009 A1 | 1/2006 |

* cited by examiner

*Primary Examiner*—Courtney Thomas
(74) *Attorney, Agent, or Firm*—Harness, Dickey & Pierce, P.L.C.

(57) ABSTRACT

It is proposed to estimate the scattered radiation on the basis of a sinogram, which is measured in any case. In at least one embodiment, a method includes determining the potential scattering site for each measuring beam from the object tangents in the sinogram and calculating the scattered intensity from the primary radiation striking the scattering site and the angle ratios of scattering beam, object tangent and measuring beam. Also proposed, in at least one embodiment, is an X-ray CT having at least bifocal detector systems and a control and computer unit for producing tomographic pictures, the control and arithmetic unit of which contains a program code that, upon being executed, carries out the method.

19 Claims, 3 Drawing Sheets

METHOD FOR SCATTERED RADIATION CORRECTION IN THE CASE OF AN X-RAY CT, AND X-RAY CT FOR APPLYING THIS METHOD

PRIORITY STATEMENT

The present application hereby claims priority under 35 U.S.C. §119 on German patent application number DE 10 2006 019 923.5 filed Apr. 28, 2006, the entire contents of which is hereby incorporated herein by reference.

FIELD

Embodiments of the invention generally relate to a method for scattered radiation correction. For example, they may relate to a method for scattered radiation correction in the case of an X-ray CT (CT=computer tomograph) having at least two radiation sources that are arranged with an angular offset, rotate about an object and emit onto the object beams whose changes in intensity upon passage through the object are measured, wherein each beam also produces laterally directed scattered radiation at the object that is measured in addition to the intensity of a directed measuring beam and leads to a corruption of the measured data, wherein, furthermore, before the reconstruction, the measured data, which are obtained on the basis of a currently recorded sinogram of the object, are subjected to a scattered radiation correction.

BACKGROUND

It is generally known that during CT examinations scattered radiation effects are produced that lead to inaccuracies in the measurement of the absorption of X-radiation. Looking first at this effect in unifocal detector systems, the problem of scattered radiation here becomes larger the wider the beam fan used is expanded, since the sites at which scattered radiation is produced increase correspondingly. In the case of such CT systems, these known effects are counteracted by fitting in front of the detector so called scattered radiation collimators that expose in front of each detector element only the direct radiation direction between detector element and focus, and largely shade all the other directions. Such scattered radiation collimators are also used with the bifocal or multifocal detector systems. However, these scattered radiation collimators cannot diminish the scattered radiation that are produced by beams of another focus arranged with an angular offset and whose alignment has the same spatial orientation as the actual direct beam that originates from a focus opposite the detector and whose intensity is to be measured.

There is, furthermore, a complication that the examined objects—which are preferably different patients in this case—vary in their spatial configuration from examination to examination, and so, when the aim is to examine with adequate safety, the scattered radiation generated can only be determined individually. Moreover, the examined object is to be subjected during an examination only to the lowest possible dose, and so numerous test scans that could be used only to determine the scattered radiation should be avoided.

SUMMARY

In at least one embodiment of the invention, a method is disclosed for scattered radiation correction in the case of an X-ray CT examination which manages without additional test scans while nevertheless adequately taking account of the individual proportions of the examined object.

The inventors have realized that it is possible to use appropriate analysis of a sinogram recorded during a CT scan in order to determine the sites of the production of scattered radiation on an object being examined, doing so with sufficient accuracy so as to determine, on the basis of knowledge of a scattering beam incident there, and of the direction of the scattered beam measured thereon, the scattered beam component of the measured radiation intensity in the case of a number of radiation sources, arranged with a mutual angular offset, during a CT examination.

From a consideration of the respective measuring system with its radiation source and its detector with the detector elements it is possible, starting from each detector element, to find the measuring beam assigned thereto as a connection to the radiation source, the site of origin of the additionally measured scattered radiation necessarily also lying on this connecting line. This condition assumes, however, that the detector has radiation collimators that actually admit only beams on the line between detector element and radiation source to be incident on the detector, whereas other radiation directions are masked out by the collimators.

Use is made here, in addition, of the knowledge that scattered radiation exists chiefly in edge regions of the object, specifically on the side facing the focus that emits the radiation producing scattered radiation, and on the side facing the detector there.

Once this site of potential production of scattered radiation has been found, a search is made for the beam, producing scattered radiation, of the radiation source arranged with an offset, and the knowledge of the intensity of this scattering beam is used to determine the quantity of the scattered radiation, and thus the measured scattered radiation component. This can be done, for example, by estimating the scattered radiation component in direct proportion to the intensity of the scattering beam. However, it is also possible to take account of the angle dependencies in the case of the irradiation of the scattering beam relative to the incidence angle of the scattered radiation, and thus to obtain more accurate data.

In accordance with at least one embodiment, the inventors propose to estimate the scattered radiation on the basis of the sinogram, measured in any case, in a two-stage method by executing the following method steps:

1. determining the potential scattering sites for each measuring beam from the object tangents in the sinogram; and
2. calculating the scattering intensity from the primary radiation (scattered radiation) striking the scattering site, and from the angle ratios of scattering beam, object tangents and measuring beam.

Furthermore, in at least one embodiment, it is proposed to improve the method for scattered radiation correction in the case of an X-radiation CT having at least two radiation sources that are arranged with an angular offset, rotate about the object and emit onto the object beams whose changes in intensity upon passage through the object are measured, wherein each beam also produces laterally directed scattered radiation at the object that is measured in addition to the intensity of a directed measuring beam and leads to a corruption of the measured data. Furthermore, wherein before the reconstruction, the measured data, which are obtained on the basis of a currently recorded sinogram of the object, are subjected to a scattered radiation correction.

One inventive improvement of at least one embodiment of this method resides in that in order to determine the scattered radiation component of measured radiation intensities, the profile of a resulting measuring beam is determined for each projection angle and each detector element of a detector, the potential production site of scattered radiation is determined from this profile and the sinogram of the object, a scattering beam running through this production site is determined, and the scattered radiation component of the measured radiation intensity is determined by taking account of the actual intensity of the scattering beam.

At least one embodiment of this inventive method now enables an accurate and individually object-referred determination of the scattered radiation component when measuring the radiation absorption owing to a number of radiation sources arranged with an angular offset, without there being a need for additional test scans to determine the scattered radiation component.

In a particular design of the method according to at least one embodiment of the invention, the inventors further propose that the following method steps be carried out:
- the object silhouettes are determined in the currently recorded sinogram of at least one slice plane,
- the tangential beam defined by the object silhouette is determined,
- a measuring beam passing through the point of intersection of object silhouette and tangential beam is determined,
- at least one beam from the at least one second radiation source and running through the point intersection of object silhouette and tangential beam is determined,
- the incidence angle between tangential beam and scattering beam, and the exit angle between tangential beam and measuring beam are determined, and
- the scattered radiation intensity is subsequently calculated on the basis of the different incidence angle and exit angle and the intensity of the scattering beam.

According to at least one embodiment of the invention, the object silhouette can be determined, for example, by a prescribed threshold value of the measured radiation intensity, or—as a more robust variant—by a prescribed threshold value of an integral, advancing from outside to inside, of the measured radiation intensity in the sinogram.

The functional dependence between the generated scattered radiation intensity and the incidence angle and exit angle to the intensity of the scattering beam can be determined both empirically, that is to say by experiments, and by statistical calculations or can be calculated with the aid of physical models.

In a further design of at least one embodiment, the inventors propose in this case that the scattered radiation intensity produced at the object silhouette is calculated with the aid of the following formula:

$$I_S = I_0 f(\phi_S) \frac{\sin\phi_S}{\sin\phi_M} f(\phi_M) g(\pi - \phi_S - \phi_M),$$

as follows:
$I_S$=intensity of the generated scattered radiation;
$I_0$=intensity of the direct radiation generating scattered radiation;
$f(\phi_S)$=functional dependence of the scattered radiation intensity on $\phi_S$;
$f(\phi_M)$=functional dependence of the scattered radiation intensity on $\phi_M$;
$g(\pi-\phi_S-\phi_M)$=functional dependence of the scattering on the angle between the incident beam ($\phi_S$) and scattered beam ($\phi_M$);
$\phi_S$=incidence angle between tangential beam ($S_T$) and scattering beam ($S_S$); and
$\phi_M$=exit angle between tangential beam ($S_T$) and measuring beam ($S_M$).

In a simple variant, it is possible here to select at least one of the functions $f(\phi_S)$, $f(\phi_M)$ or $g(\pi-\phi_S-\phi_M)$ as constant, preferably being equal to 1. However, it is also possible to determine these functions individually or as a whole with the aid of empirical results.

A particular variant of the determination of these functions by way of empirical results can reside in that these are varied until low-artifact tomographic data are produced in the reconstruction. This search for optimum functions need not, however, be carried out for each object examined, but it suffices for this purpose to make a one-off determination of the optimum function, which can then be applied for different objects investigated.

The inventors further propose, in at least one embodiment, that the determined scattered radiation components are smoothed with the aid of a kernel whose size corresponds to the aperture of the collimator per detector element of the detector used. This takes account of the fact that the collimator has a finite aperture.

The inventors propose, furthermore, that at least one embodiment of this method is applied only to an undersampled set of measuring channels or a portion of projections. The computing time for determining the scattered radiation components is substantially reduced thereby. Such an approach is possible by all means, since it can be assumed that the size of the scattered radiation component changes only slowly over the measuring channels, and that no abrupt or discontinuous variations occur with reference to the scattered radiation component.

BRIEF DESCRIPTION OF THE DRAWINGS

The invention is described in more detail below with reference to the example embodiments and with the aid of the figures, only the features required for understanding the invention being illustrated, and the following reference symbols being used: 1: CT system; 2: first X-ray tube; 3: first detector; 4: second X-ray tube; 5: second detector; 6: gantry housing; 7: patient; 8: movable patient couch; 9: system axis; 10: control and arithmetic unit; 11: memory of the control and arithmetic unit; $D_1$: first detector; $D_2$: second detector; $F_1$: first focus; $F_2$: second focus; G: object silhouette; $G_S$: threshold value of the object silhouette; $K_1$: first collimator; $K_2$: second collimator; L: section through a sinogram for a projection angle; p: measuring channel; $Prg_1$-$Prg_n$: computer programs; $S_{1,i}$: rays of the first beam; $S_{2,i}$: rays of the second beam; $S_M$: measuring beam; $S_S$: scattering beam; $S_T$: tangential beam; $S_{1\rightarrow 2}$: scattered radiation from the first focus detector system into the second detector; $S_{2\rightarrow 1}$: scattered radiation from the second focus detector system into the first detector; $T_1$, $T_2$: measuring channel of the object silhouette; Z: scattering site; a: projection angle; μ: absorption; $μ_T$: function of the absorption over the measuring channels in the sinogram; $\phi_M$: exit angle; $\phi_S$: incidence angle.

In detail.

DETAILED DESCRIPTION OF THE EXAMPLE EMBODIMENTS

Figure 1:
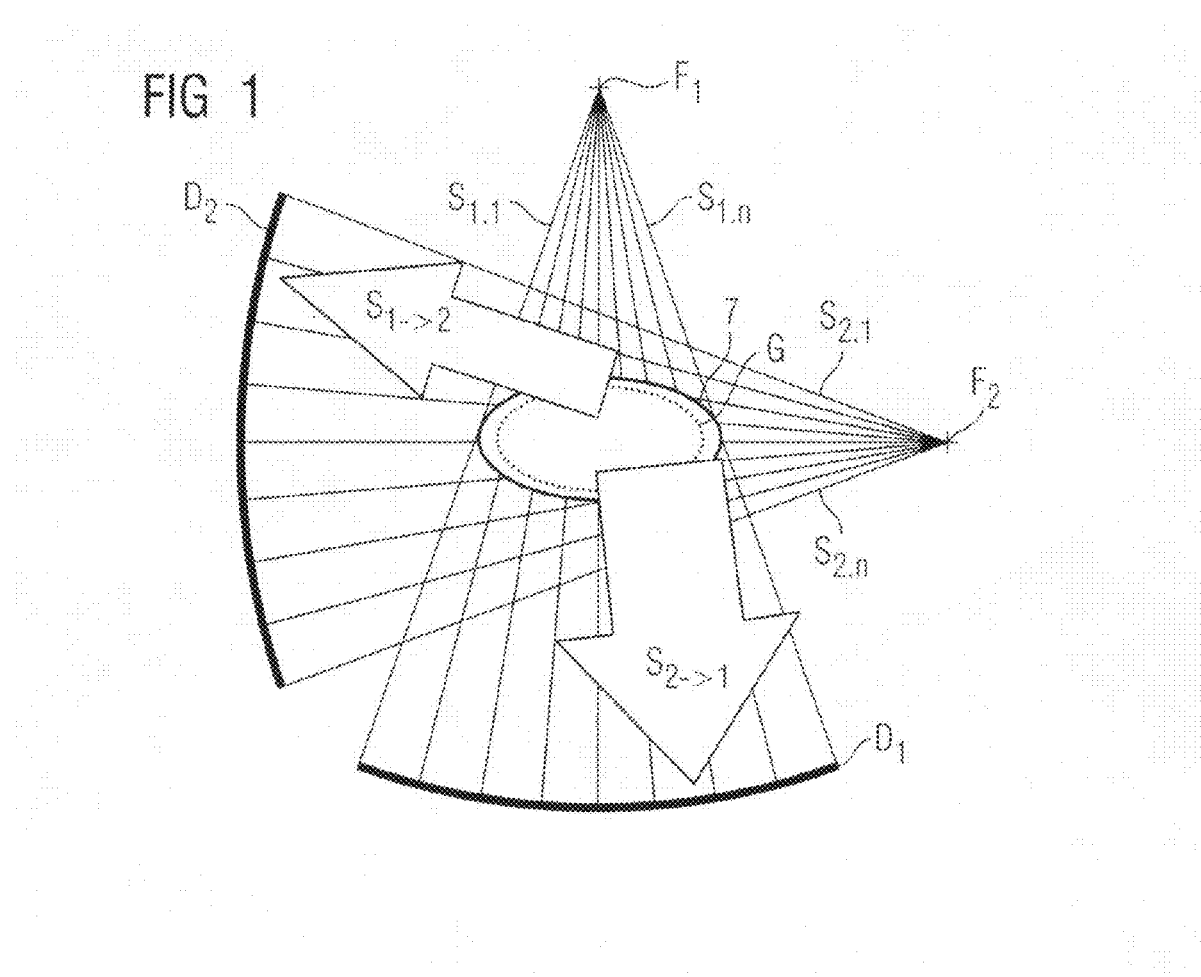
FIG. 1 shows a diagrammatic sectional illustration of the scanning of a patient with the aid of two focus detector systems arranged with an angular offset.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

FIG. 1 shows a diagrammatic sectional illustration of the scanning of a patient 7 with the aid of bifocal detector systems arranged at an angle offset of 90° to one another. The first focus detector system has a focus $F_1$ and an opposite detector $D_1$, a beam $S_{1,i}$ emanating from the first focus $F_1$, penetrating the patient 7 and being measured on the opposite detector $D_1$ with reference to its intensity. The absorption of the radiation by the patient 7 can be determined from the difference between the initial intensity and the intensity striking the detector.

Arranged at a right angle thereto is a second focus detector system with a second focus $F_2$ and a second detector $D_2$. Here, as well, there is produced at the focus $F_2$ a beam $S_{2,i}$ that is directed onto the opposite detector $D_2$, and whose intensity is measured after the penetration of the patient, it being possible here, as well, to determine the absorption of the patient in the respective beam path from the ratio of the initial intensity and the intensity measured in the detector.

The problem of such measuring systems arranged simultaneously with an angular offset resides in that when striking the patient each beam $S_{1,i}$ and $S_{2,i}$ simultaneously produces a scattered radiation that is respectively detected in relation to the direct measured radiation by the measuring system arranged with an angular offset therefrom, and in so doing apparently increases the measured radiation intensity of the respective beam to be measured directly, or, with a reverse conclusion, to an apparently reduced absorption of the respective measuring beam upon passage through the patient. The scattered radiation produced is represented diagrammatically in the illustration by two large arrows denoted by $S_{1 \to 2}$ and $S_{2 \to 1}$.

In addition, the object silhouette G is further identified by a dotted line in FIG. 1 at the diagrammatic illustration of the patient 7. This object silhouette defines the object depth at which scattered radiation is produced substantially or on average. In the sinogram illustration shown later, this corresponds to a first absorption threshold value reached.

Figure 2:
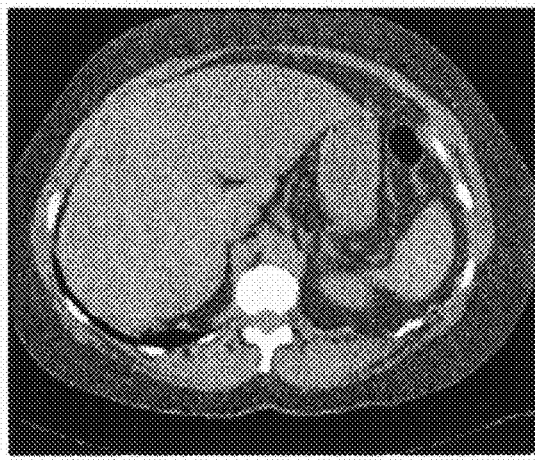
FIG. 2 shows a CT section of an abdomen.
Figure 3:
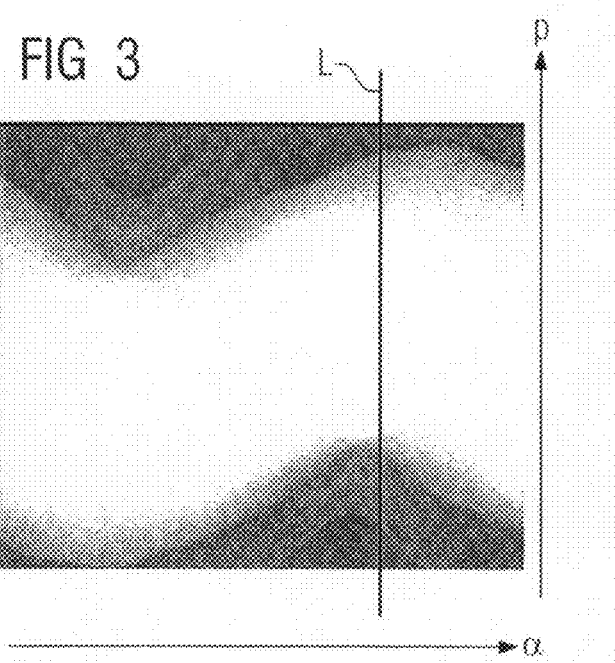
FIG. 3 shows a sinogram of the abdomen from FIG. 2.

FIG. 2 shows an exemplary CT sectional picture of an abdomen for which FIG. 3 illustrates the sinogram data from the scan of a complete revolution for a detector row. The ordinate shows the respective projection angle a in this case, while the measuring channels p of the detector row are illustrated on the abscissa.

Figure 4:
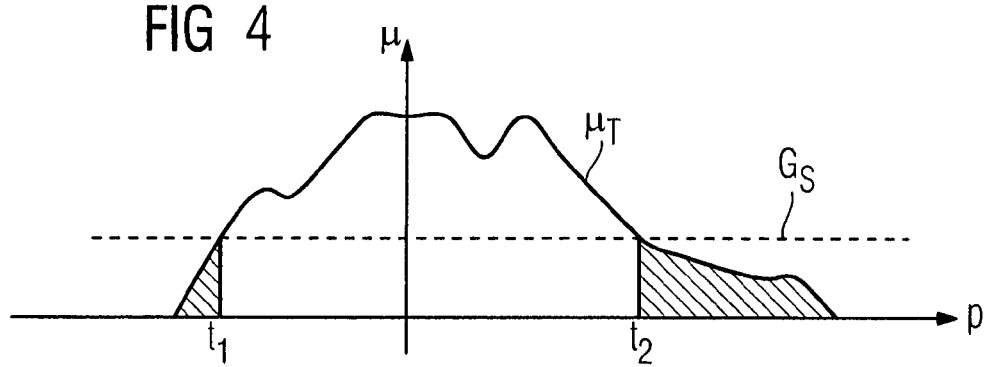
FIG. 4 shows sinogram data for a projection angle for the purpose of determining the object silhouettes.

FIG. 4 shows the absorption values of a sinogram along a section L, as shown in FIG. 3, the absorption values $\mu_T$ having been plotted over the measuring channels. If the center of this sinogram is approached from the left or right, the absorption values at the sites $t_1$ and $t_2$ reach a predetermined threshold value that is denoted in this publication as object silhouette. By varying this threshold value, this object silhouette can be set appropriately according to the actual ratios during the production of scattering as a function of the energy spectrum for the radiation.

Alternatively, it is also possible to use a threshold value for a maximum surface integral of the absorption values that is reached, instead of the threshold value for the absorption values. This prevents the object silhouette migrating inward given unfavorable ratios, and the method becomes more robust overall.

Figure 5:
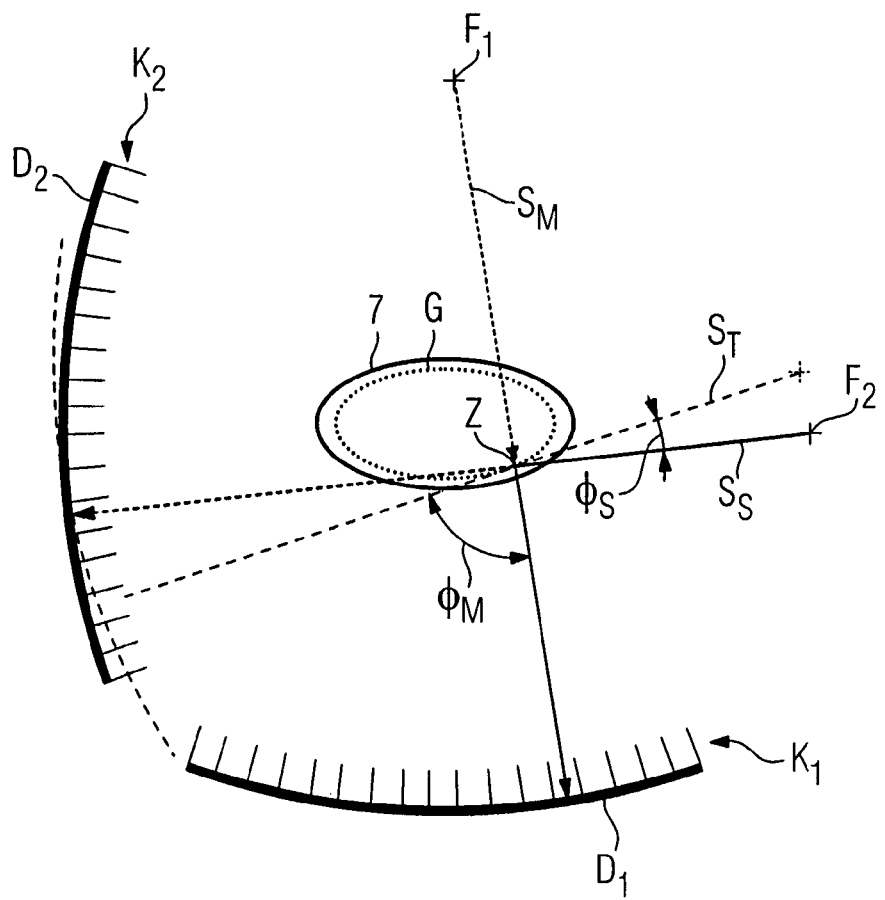
FIG. 5 shows a diagrammatic illustration of the determination of the site of the production of the scattered radiation.

FIG. 5 further illustrates the measuring situation with the bifocal detector systems arranged with an angular offset, the collimators $K_1$ and $K_2$ also being indicated in each case at the corresponding detectors in order to illustrate their action. A measuring beam $S_M$ goes from the focus $F_1$ to the opposite detector $D_1$ and penetrates the patient 7 in this case. For this measuring beam $S_M$, is depicted at the detector-side point of intersection of the measuring beam $S_M$ and the object silhouette G the tangential beam $S_T$ running tangentially here to the object silhouette, it being assumed that the main center Z of the production of scattered radiation (scattering site) also lies at this site, and so it is possible to define the scattering beam $S_S$, which runs from the focus $F_2$ of the focus detector system, arranged with an angular offset, to the detector $D_2$. The two angles $\phi_M$ between the measuring beam $S_M$ and the tangential beam $S_T$ and $\phi_S$ between the measuring beam $S_M$ and the scattering beam $S_S$ are additionally plotted.

In the method according to an embodiment of the invention, the transverse scattering in a multitube CT is estimated solely by the evaluation of the sinogram, the calculation being performed essentially in two steps:
1. calculating the tangent angle and, if appropriate, the intensities of the scattering beams for all measuring beams from the object silhouettes in the sinogram; and
2. calculating the scattering intensities for a measuring beam fan for the tangent angles of all the measuring beams.

The measuring beam is defined by the scattering beam collimator. The tangential beams $S_T$ are given in the sinogram by virtue of the fact that the attenuation D(p) in them firstly or finally reaches a specific attenuation value. Once all the tangential beams are known, it is possible to determine the tangent angle for each measuring beam, in which case it holds that: the tangential beam for a measuring beam is that beam which cuts the measuring beam furthest from the detector. The tangential beam $S_T$ is thus known for each measuring beam, and so also is the exit angle $\phi_M$. In addition, the distance of the point of intersection of the tangential beam from the detector can be determined for each measuring beam.

It is possible therefrom then to determine the beam, leading to scattering, of the respective non-directly irradiating focus, and to calculate the intensity of the scattering beam, if appropriate. Such a determination of the intensity of the beam can be particularly important in the case of which, for example owing to a shape filter, the radiation intensity is a function of the fan angle, or there is a dependence on the focus angle because, for example, a dose modulation is present during scanning. Considering, now, the illustration in FIG. 5 the following relationship is yielded for the intensity $I_S$ of the scattering beam on the tangential beam:

$$I_S = I_0 \cdot f(\phi_S) \cdot \sin \phi_S, \text{ wherein}$$

$I_0$ represents the intensity of the incident scattering beam, and $f(\phi_S)$ represents a function that is to be determined empirically and could, for example, take account of the fact that for very small angles $\phi_S$ the beam is already clearly attenuated before scattering. In the simplest case, this function could be set as $f(\phi_S)=1$.

The scattering intensity $I_M$ reaching into the measuring beam can then be calculated with the aid of the following relationship:

$$I_M = I_S \cdot \frac{1}{\sin \phi_M} f(\phi_M) \cdot g(\pi - \phi_S - \phi_M).$$

The result after insertion of the relationship for $I_S$ is:

$$I_M = I_0 \cdot f(\phi_S) \frac{\sin \phi_S}{\sin \phi_M} \cdot f(\phi_M) \cdot g(\pi - \phi_S - \phi_M)$$

Here, the function $f(\phi_M)$ takes account of the absorption of the scattering beam in the tissue for small angles $\phi_M$. The function $g(\pi-\phi_S-\phi_M)$ takes account of the scattering intensity, in particular of the differential effective cross section, that is to say dependence of the scattering intensity on incidence angle $\phi_S$ and exit angle $\phi_M$.

In order to take account of the fact that the collimator of the measuring beam has a finite aperture, it is possible, in addition, for the scattering intensity determined for all the channels to be smoothed with the aid of a kernel corresponding to this aperture.

Furthermore, it is possible to save computing time by calculating not all the measuring channels, but only an undersampled subset of the measuring channels, also only an undersampled portion of the projections, it being possible later to interpolate intermediate values of the scattering intensity.

Figure 6:
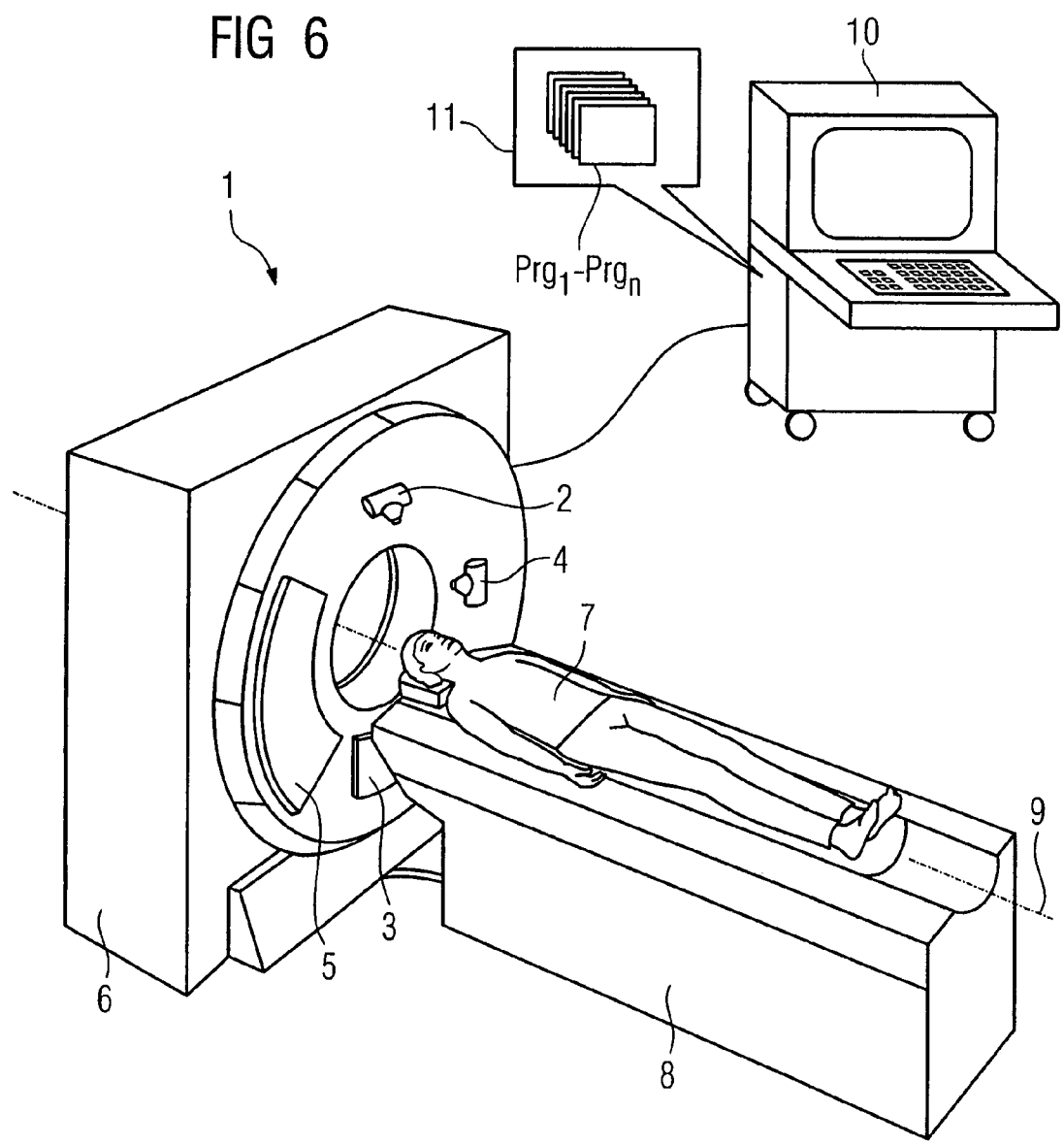
FIG. 6 shows a CT system with a control and computer unit for carrying out the method according to an embodiment of the invention.

FIG. 6 illustrates a computer tomography system 1 according to an embodiment of the invention, in which bifocal detector systems are arranged in a gantry housing 6. The first focus detector system is formed by the X-ray tube 2 and the opposite detector 3, while the second focus detector system is formed by the X-ray tube 4 and the opposite detector 5. For the purpose of scanning, the patient 7 or, if appropriate, another object can be pushed through the scanning area of the bifocal detector systems. In the illustration shown, this purpose is served by a movable patient couch 8 on which the patient 7 is moved during the scan along the system axis 9 such that a spiral scanning takes place relative to the patient. However, it may be pointed out that the method according to an embodiment of the invention is also possible in conjunction with purely circular scans and sequential movement of the object to be scanned along the system axis, a purely circular scanning of the entire examination area also being possible by making use of correspondingly wide multirow detectors.

The control of the CT system and evaluation of the detector data with reconstruction of volume data or tomographic sectional images can take place according to an embodiment of the invention in the control and computer unit 10, in whose memory 11 there are stored the corresponding programs $Prg_1$ to $Prg_n$ that, upon being executed, also carry out, inter alia, the method according to an embodiment of the invention for scattered radiation correction.

It goes without saying that the abovementioned features of an embodiment of the invention can be used not only in the respectively specified combination, but also in other combinations or on their own, without departing from the scope of the invention.

At least one embodiment of the invention thus proposes overall to estimate the scattered radiation on the basis of the sinogram measured in any case, doing so in a two-stage method having the following method steps:

1. determining the potential scattering site for each measuring beam from the object tangents in the sinogram; and
2. calculating the scattering intensity from the primary radiation striking the scattering site and the angle ratios of scattering beam, object tangent and measuring beam.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a build-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scattered radiation correction for an X-ray computer tomograph including at least two X-ray sources, the scattered radiation being determined on the basis of a sinogram currently being measured from a scanned object, of the method comprising:
   determining a potential scattering site for each measuring beam from radiation tangents, determinable in a sinogram, to the scanned object; and
   calculating an intensity of the scattered radiation from a scattering beam striking the determined scattering site, and angle ratios of the scattering beam, the radiation tangent to the examination object and the measuring beam.

2. The method as claimed in claim 1, wherein at least two radiation sources, that are arranged with an angular offset and rotate about the object, are used to emit onto the object beams whose changes in intensity upon passage through the object are measured, wherein
   each beam also produces laterally directed scattered radiation at the object that is measured in addition to the intensity of a directed measuring beam and leads to a corruption of the measured data, and
   before reconstruction, the measured data, which are obtained on the basis of a currently recorded sinogram of the object, are subjected to a scattered radiation correction,
   in order to determine a scattered radiation component of measured radiation intensities, a profile of a resulting measuring beam is determined for each projection angle and each detector element of a detector,
   the potential production site of scattered radiation is determined from the profile and the sinogram of the object,
   a scattering beam running through this production site is determined, and
   the scattered radiation component of the measured radiation intensity is calculated by taking account of the actual intensity of the scattering beam.

3. The method as claimed in claim 1, wherein
   an object silhouette is determined in the currently recorded sinogram of at least one slice plane,
   the tangential beam defined by the object silhouette is determined,
   a measuring beam passing through the point of intersection of object silhouette and tangential beam is determined,
   at least one beam from the at least one second radiation source and running through the point of intersection of object silhouette and tangential beam is determined,
   the incidence angle between tangential beam and scattering beam, and the exit angle between tangential beam and measuring beam are determined, and
   the scattered radiation intensity is subsequently calculated on the basis of the different incidence angle and exit angle and the intensity of the scattering beam.

4. The method as claimed in claim 3, wherein the object silhouettes are determined by a prescribed threshold value of the measured radiation intensity.

5. The method as claimed in claim 3, wherein the object silhouettes are determined by a prescribed threshold value of an integral value, advancing from outside to inside, of the measured radiation intensity in the sinogram.

6. The method as claimed claim 2, wherein the functional dependence between the generated scattered radiation intensity, the incidence angle and exit angle and the intensity of the scattering beam is determined empirically in advance.

7. The method as claimed in claim 2, wherein the functional dependence between the generated scattered radiation intensity, the incidence angle and exit angle and the intensity of the scattering beam is determined by statistical calculations in advance.

8. The method as claimed in claim 2, wherein the functional dependence between the generated scattered radiation intensity, the incidence angle and exit angle and the intensity of the scattering beam is calculated analytically in advance with the aid of physical models.

9. The method as claimed in claim 2, wherein the scattered radiation intensity produced at the object silhouette is calculated with the aid of the following formula:

$$I_S = I_0 f(\phi_S) \frac{\sin\phi_S}{\sin\phi_M} f(\phi_M) g(\pi - \phi_S - \phi_M),$$

as follows:
   $I_S$=intensity of the generated scattered radiation;
   $I_0$=intensity of the direct radiation generating scattered radiation;
   $f(\phi_S)$=functional dependence of the scattered radiation intensity on $\phi_S$;
   $f(\phi_M)$=functional dependence of the scattered radiation intensity on $\phi_M$;
   $g(\pi-\phi_S-\phi_M)$=functional dependence of the scattering of the incidence angle ($\phi_S$) and exit angle ($\phi_M$);
   $\phi_S$=incidence angle between tangential beam ($S_T$) and scattering beam ($S_S$); and
   $\phi_M$=exit angle between tangential beam ($S_T$) and measuring beam ($S_M$).

10. The method as claimed in claim 9, wherein at least one of the functions $f(\phi_S)$, $f(\phi_M)$ and $g(\pi-\phi_S-\phi_M)$ is selected as constant.

11. The method as claimed in claim 9, wherein at least one of the functions $f(\phi_S)$, $f(\phi_M)$ and $g(\pi-\phi_S\phi_M)$ is varied until low-artifact tomographic data are produced.

12. The method as claimed in claim 1, wherein the determined scattered radiation components are smoothed with the aid of a kernel whose size corresponds to the aperture of the collimator per detector element of the detector used.

13. The method as claimed in claim 1, wherein the method is applied only to an undersampled set of the measuring channels or a subset of the projections.

14. The method as claimed in claim 2, wherein
   the object silhouette is determined in the currently recorded sinogram of at least one slice plane,
   the tangential beam defined by the object silhouette is determined,
   a measuring beam passing through the point of intersection of object silhouette and tangential beam is determined,
   at least one beam from the at least one second radiation source and running through the point of intersection of object silhouette and tangential beam is determined,
   the incidence angle between tangential beam and scattering beam, and the exit angle between tangential beam and measuring beam are determined, and
   the scattered radiation intensity is subsequently calculated on the basis of the different incidence angle and exit angle and the intensity of the scattering beam.

15. The method as claimed in claim 14, wherein the object silhouettes are determined by a prescribed threshold value of the measured radiation intensity.

16. The method as claimed in claim 14, wherein the object silhouettes are determined by a prescribed threshold value of an integral value, advancing from outside to inside, of the measured radiation intensity in the sinogram.

17. A computer readable medium including program segments for, when executed on a computer device, causing the computer device to implement the method of claim 1.

18. An X-ray CT comprising:
at least one bifocal detector system; and
a control and arithmetic unit to produce tomographic pictures, the control and arithmetic unit containing program code that, upon being executed, carries out the following,
   determining a potential scattering site for each measuring beam from radiation tangents, determinable in a sinogram, to a scanned object, and
   calculating an intensity of scattered radiation from a scattering beam striking the determined scattering site, and angle ratios of the scattering beam, the radiation tangent to the examination object and the measuring beam.

19. An X-ray computer tomograph, comprising:
at least two X-ray sources, wherein scattered radiation from the at least two X-ray sources is determined on the basis of a sinogram currently being measured from a scanned object;
means for determining a potential scattering site for each measuring beam from radiation tangents, determinable in a sinogram, to the scanned object; and
means for calculating an intensity of the scattered radiation from a scattering beam striking the determined scattering site, and angle ratios of the scattering beam, the radiation tangent to the examination object and the measuring beam.

* * * * *